US012315201B2

(12) United States Patent
Abbey et al.

(10) Patent No.: US 12,315,201 B2
(45) Date of Patent: May 27, 2025

(54) AUTOMATED METHOD OF IDENTIFYING A STRUCTURE

(71) Applicant: LA TROBE UNIVERSITY, Melbourne (AU)

(72) Inventors: Brian Abbey, Melbourne (AU); Eugeniu Balaur, Melbourne (AU)

(73) Assignee: LA TROBE UNIVERSITY, Melbourne (AU)

( * ) Notice: Subject to any disclaimer, the term of this patent is extended or adjusted under 35 U.S.C. 154(b) by 374 days.

(21) Appl. No.: 17/297,980

(22) PCT Filed: Nov. 29, 2019

(86) PCT No.: PCT/IB2019/060310
§ 371 (c)(1),
(2) Date: May 27, 2021

(87) PCT Pub. No.: WO2020/110072
PCT Pub. Date: Jun. 4, 2020

(65) Prior Publication Data
US 2022/0092824 A1    Mar. 24, 2022

(30) Foreign Application Priority Data
Nov. 29, 2018    (AU) ................ 2018904551

(51) Int. Cl.
*G06T 7/90* (2017.01)
*G01N 21/25* (2006.01)
*G01N 33/483* (2006.01)

(52) U.S. Cl.
CPC ............ *G06T 7/90* (2017.01); *G01N 21/255* (2013.01); *G01N 33/4833* (2013.01); *G01N 2021/258* (2013.01); *G06T 2207/10056* (2013.01)

(58) Field of Classification Search
CPC ............ G06T 7/90; G06T 2207/10056; G06T 2207/10024; G06T 2207/20084;
(Continued)

(56) References Cited

U.S. PATENT DOCUMENTS 5,836,872 A * 11/1998 Kenet ................... G06T 7/0012
382/128
6,404,916 B1    6/2002 De La Torre-Bueno
(Continued)

FOREIGN PATENT DOCUMENTS

CN    1582394 A    2/2005
CN    1957245 A    5/2007
(Continued)

OTHER PUBLICATIONS

Mingguang Shan Refractive index variance of cells and tissues measured by quantitative phase imaging vol. 25 Issue 2 p. 1573-1581 Published on 2017 (Year: 2017).*
(Continued)

*Primary Examiner* — Nizar N Sivji
(74) *Attorney, Agent, or Firm* — Knobbe, Martens, Olson & Bear, LLP

(57) ABSTRACT

An automated method of identifying a structure in a sample is disclosed. The method includes receiving at least one digital image of a sample wherein at least one localised structural property of the sample is visible in the image based on the colour of received light. The method involves processing the at least one image, based on the received colour information to selectively identify said structure. The method can include colour and/or morphology based image analysis.

18 Claims, 12 Drawing Sheets

(58) Field of Classification Search
CPC ......... G06T 2207/30024; G06T 7/0012; G06T 2207/30068; G06T 2207/30096; G01N 21/255; G01N 33/4833; G01N 2021/258; G06V 20/69; G06V 2201/032; G06N 3/08; G16H 30/40
See application file for complete search history.

(56) References Cited

U.S. PATENT DOCUMENTS

| | | | |
|---|---|---|---|
| 6,650,357 | B1 | 11/2003 | Richardson |
| 8,154,722 | B2 | 4/2012 | Yamada et al. |
| 8,536,545 | B2 | 9/2013 | Wu et al. |
| 8,687,180 | B2 | 4/2014 | Cohen |
| 9,304,234 | B2 | 4/2016 | Liu et al. |
| 9,482,784 | B2 | 11/2016 | Yen et al. |
| 9,675,288 | B2 | 6/2017 | Yamakawa et al. |
| 9,744,793 | B2 | 8/2017 | Petiton et al. |
| 10,185,137 | B2 | 1/2019 | Dai et al. |
| 10,768,105 | B1 | 9/2020 | Mohan et al. |
| 11,150,038 | B1 | 10/2021 | Poole et al. |
| 11,506,881 | B2 | 11/2022 | Balaur et al. |
| 11,545,237 | B2 | 1/2023 | Meyer et al. |
| 11,774,361 | B2 | 10/2023 | Fereidouni et al. |
| 11,798,300 | B2 | 10/2023 | Cotte et al. |
| 2002/0115224 | A1 | 8/2002 | Rudel et al. |
| 2003/0096302 | A1 | 5/2003 | Yguerabide et al. |
| 2005/0136549 | A1* | 6/2005 | Gholap ............ G06V 20/695 436/501 |
| 2007/0153267 | A1 | 7/2007 | Wang et al. |
| 2007/0178607 | A1 | 8/2007 | Prober et al. |
| 2008/0099667 | A1 | 5/2008 | Stark et al. |
| 2008/0252894 | A1 | 10/2008 | Lakowicz et al. |
| 2008/0252984 | A1 | 10/2008 | Lee et al. |
| 2008/0274905 | A1 | 11/2008 | Greene |
| 2009/0060303 | A1* | 3/2009 | Douglass ........... G02B 21/244 382/128 |
| 2009/0153866 | A1 | 6/2009 | Yamamichi et al. |
| 2010/0062422 | A1 | 3/2010 | Ausserre |
| 2010/0142259 | A1 | 6/2010 | Drindic et al. |
| 2010/0254589 | A1* | 10/2010 | Gallagher .......... G06V 20/695 382/133 |
| 2010/0264032 | A1 | 10/2010 | Bazant |
| 2010/0290692 | A1* | 11/2010 | Macaulay ............ G06T 7/0012 382/133 |
| 2010/0291575 | A1 | 11/2010 | Shamah et al. |
| 2011/0157593 | A1 | 6/2011 | Miyadera et al. |
| 2012/0113424 | A1 | 5/2012 | Suda et al. |
| 2013/0065777 | A1 | 3/2013 | Altug et al. |
| 2013/0279789 | A1* | 10/2013 | Elter ................. G06V 10/56 382/134 |
| 2014/0131559 | A1 | 5/2014 | Yen et al. |
| 2014/0168651 | A1 | 6/2014 | Guo |
| 2014/0206101 | A1 | 7/2014 | Liu et al. |
| 2014/0327913 | A1 | 11/2014 | Pacifici et al. |
| 2014/0349278 | A1 | 11/2014 | Yamamoto |
| 2015/0002843 | A1 | 1/2015 | Yokogawa |
| 2015/0177140 | A1 | 6/2015 | Guo |
| 2016/0108256 | A1 | 4/2016 | Yang et al. |
| 2016/0110584 | A1* | 4/2016 | Remiszewski ........ G06V 20/69 382/133 |
| 2016/0258114 | A1 | 9/2016 | Firth et al. |
| 2016/0290926 | A1* | 10/2016 | Notingher ............ G01N 21/65 |
| 2016/0306157 | A1 | 10/2016 | Rho et al. |
| 2016/0334398 | A1* | 11/2016 | Weissleder ......... G01N 33/553 |
| 2016/0355869 | A1 | 12/2016 | Blair et al. |
| 2016/0357026 | A1 | 12/2016 | Astratov et al. |
| 2016/0370290 | A1 | 12/2016 | Raphael et al. |
| 2018/0045644 | A1 | 2/2018 | Baumgold |
| 2018/0066937 | A1 | 3/2018 | Ikeda et al. |
| 2018/0107038 | A1 | 4/2018 | Chen et al. |
| 2018/0202918 | A1 | 7/2018 | Tanaka et al. |
| 2019/0071779 | A1* | 3/2019 | Hamers ............... C23C 16/0281 |
| 2019/0154652 | A1* | 5/2019 | Ghosh ................ G02B 21/16 |
| 2019/0195809 | A1 | 6/2019 | Agarwal et al. |
| 2019/0317011 | A1 | 10/2019 | Hu |
| 2020/0116987 | A1 | 4/2020 | Kleppe et al. |
| 2020/0142173 | A1 | 5/2020 | Balaur et al. |
| 2020/0264043 | A1 | 8/2020 | Allen |
| 2020/0285043 | A1 | 9/2020 | Nyga et al. |
| 2020/0319382 | A1 | 10/2020 | Guo et al. |
| 2020/0326282 | A1 | 10/2020 | Singamaneni et al. |
| 2021/0181391 | A1 | 6/2021 | Subramaniyam et al. |
| 2022/0059866 | A1 | 2/2022 | Mukherjee et al. |
| 2022/0091307 | A1 | 3/2022 | Abbey et al. |
| 2022/0091407 | A1* | 3/2022 | Abbey ................ G02B 5/008 |
| 2022/0092824 | A1 | 3/2022 | Abbey et al. |
| 2022/0215533 | A1 | 7/2022 | Abbey et al. |
| 2022/0235415 | A1 | 7/2022 | Fretes |
| 2022/0381984 | A1 | 12/2022 | Li et al. |
| 2023/0266291 | A1 | 8/2023 | Myrick |

FOREIGN PATENT DOCUMENTS

| | | | |
|---|---|---|---|
| CN | 101031789 A | 9/2007 | |
| CN | 101470219 | 9/2010 | |
| CN | 102317781 A | 1/2012 | |
| CN | 102460171 A | 5/2012 | |
| CN | 103018167 A | 4/2013 | |
| CN | 101952697 | 8/2014 | |
| CN | 104919299 A | 9/2015 | |
| CN | 105974571 A | 9/2016 | |
| CN | 205691505 U | 11/2016 | |
| CN | 108474874 A | 8/2018 | |
| DE | 10329195 A1 | 1/2005 | |
| DE | 102012214932 | 2/2014 | |
| EP | 2 653 903 | 10/2013 | |
| EP | 2653903 A1 * | 10/2013 | ........... G01N 21/554 |
| EP | 3 121 587 | 1/2017 | |
| EP | 2146229 | 4/2019 | |
| JP | 2001133618 | 5/2001 | |
| JP | 2007-501391 | 1/2007 | |
| JP | 2007192806 | 8/2007 | |
| JP | 2007-538264 | 12/2007 | |
| JP | 2009222401 | 10/2009 | |
| JP | 2009223123 | 10/2009 | |
| JP | 2010009025 | 1/2010 | |
| JP | 2011-53151 | 3/2011 | |
| JP | 2011-252928 | 12/2011 | |
| JP | 2012159792 | 8/2012 | |
| JP | 2013-142546 | 7/2013 | |
| JP | 2013-231682 | 11/2013 | |
| JP | 2015-12128 | 1/2015 | |
| JP | 2016212126 | 12/2016 | |
| JP | 2015-514225 | 3/2018 | |
| JP | 2018-528405 | 9/2018 | |
| JP | 2018-532132 | 11/2018 | |
| KR | 20120075189 | 12/2012 | |
| TW | 201418698 | 5/2014 | |
| WO | WO 2003/073817 | 9/2003 | |
| WO | WO 2005/017570 | 2/2005 | |
| WO | WO 2005/114298 | 12/2005 | |
| WO | WO 2008/039212 | 4/2008 | |
| WO | WO 2009/072098 | 6/2009 | |
| WO | WO-2009072098 A1 * | 6/2009 | ........... G06K 9/0014 |
| WO | WO 2009/089292 | 7/2009 | |
| WO | WO-2009089292 A1 * | 7/2009 | ........... A61B 5/0075 |
| WO | WO 2010/075033 | 7/2010 | |
| WO | WO 2010/132890 | 11/2010 | |
| WO | WO 2011/163624 | 12/2011 | |
| WO | WO 2013/089996 | 6/2013 | |
| WO | WO 2014/053955 | 4/2014 | |
| WO | WO 2015005904 | 1/2015 | |
| WO | WO 2015/056584 | 4/2015 | |
| WO | WO 2015/140362 | 9/2015 | |
| WO | WO 2015/199976 | 12/2015 | |
| WO | WO 2017/051195 | 3/2017 | |
| WO | WO-2017051195 A1 * | 3/2017 | ........... G06T 7/0012 |
| WO | WO 2017/109175 | 6/2017 | |
| WO | WO 2017/135430 | 8/2017 | |
| WO | WO 2017/161097 | 9/2017 | |
| WO | WO 2018/107038 | 6/2018 | |
| WO | WO 2018/152157 | 8/2018 | |
| WO | WO-2018152157 A1 * | 8/2018 | ........... G01N 33/49 |

(56) References Cited

FOREIGN PATENT DOCUMENTS

| WO | WO 2018/213881 | 11/2018 |
|---|---|---|
| WO | WO 2020/110069 | 6/2020 |
| WO | WO 2020/110070 | 6/2020 |
| WO | WO 2020/110071 | 6/2020 |
| WO | WO 2020/110072 | 6/2020 |

OTHER PUBLICATIONS

Lee Seung-Woo et al: "Highly Sensitive Biosensing Using Arrays of Plasmonic Au Nanodisks Realized by Nanoimprint Lithography", ACS NANO, vol. 5, No. 2, Jan. 11, 2011 (Jan. 11, 2011), pp. 897-904, XP055943779, US, ISSN: 1936-0851, DOI: 10.1021/nn102041m.

Mudachathi Renilkumar et al: "Design of a 1-7 colorimetric sensing platform using reflection mode plasmonic colour filters", Proceedings of SPIE; [vol. 10524], SPIE, US, vol. 10346, Aug. 25, 2017 (Aug. 25, 2017), pp. 103460D-103460D, XP060092566.

Balaur Eugenio et al: "Electron-beam induced diamond-like-carbon passivation of plasmonic devices", Biomedical Photonics and Optoelectronic Imaging : Nov. 8-10, 2000, Beijing, China; SPIE, Bellingham, Wash., US, vol. 9668, Dec. 22, 2015 (Dec. 22, 2015), pp. 966817-966817, XP060063550.

Langley D et al: "Dual pitch plasmonic devices for polarization enhanced colour based sensing", Proceedings of SPIE, SPIE, US, vol. 10013, Dec. 9, 2016 (Dec. 9, 2016).

Kan T et al: "Sub-micron aperture plate for intracellular calcium transient measurement", TRANSDUCERS '05 : [Jun. 5-9, 2005] ; Digest of Technical Papers, IEEE Operations Center, Piscataway, NJ, vol. 2, Jun. 5, 2005 (Jun. 5, 2005).

Shan Mingguang et al: "Refractive index variance of cells and tissues measured by quantitative phase imaging", Optics Express, [Online] vol. 25, No. 2, Jan. 23, 2017 (Jan. 23, 2017), p. 1573, XP055918186, ISSN: 1094-4087, DOI: 10.1364/OE.25.001573 Retrieved from the Internet: URL: https://www.osapublishing.org/viewmedia.cfm?URI=oe-25-2-1573> retrieved on Jul. 4, 2022].

European Supplementary Search Report for EP Application No. 19890517.6 dated Aug. 3, 2022 in 14 pages.

European Extended Search Report for EP Application No. 19889218.4 dated Aug. 9, 2022 in 10 pages.

European Search Report for EP Application No. 19889220.0 dated Aug. 12, 2022 in 14 pages.

European Search Report for EP Application No. 19890518.4 dated Aug. 4, 2022 in 9 pages.

Motevich I. G. et al: "Application of Plasmonic Silver Films in Histology for Contrast Enhancement", Journal of Applied Spectroscopy, vol. 79, No. 4, Sep. 2012 (Sep. 2012), pp. 632-636.

Wang X et al: "Self-Referenced Smartphone-Based Nanoplasmonic Imaging Platform for Colorimetric Biochemical Sensing", Analytical Chemistry, vol. 89, No. 1, Dec. 15, 2016 (Dec. 15, 2016), pp. 611-615.

Extended European Search Report for EP Application No. 19889220.0, dated Nov. 10, 2022.

Notice of Reasons for Rejection in JP Patent Application No. 2021-230110 (English translation), dated Apr. 11, 2023 in 6 pages.

Office Action for CN Application No. 201980090294.2 dated Feb. 2, 2023 and Search Report in 9 pages (no English translation available).

Notice of Reasons for Rejection in JP Patent Application No. 2021-530111, dated May 30, 2023 and English Translation, in 13 pages.

Carr, R.J.G., et al. "Submicron optical sources for single macromolecule detection." Proceedings of the SPIE, SPIE, Bellingham, VA, US, vol. 1796, Sep. 8, 1992, pp. 152-156.

Balaur, E., et al. "Continuously tunable, polarization controlled, colour palette produced from nanoscale plasmonic pixels." Scientific reports 6 (2016): 28062.

Office Action dated Aug. 22, 2023 for Chinese Patent Application No. 201980090294.2.

Office Action for Japanese Patent Application No. 2021-530110.

Office Action dated Sep. 14, 2023 for Canadian Patent Application No. 3,121,434.

Office Action dated Sep. 14, 2023 for Canadian Patent Application No. 3,121,425.

U.S. Appl. No. 17/297,974, filed May 27, 2021, Abbey et al.
U.S. Appl. No. 17/297,977, filed May 27, 2021, Abbey et al.
U.S. Appl. No. 17/297,979, filed May 27, 2021, Abbey et al.

Altunbay, D et al. Color Graphs for Automated Cancer Diagnosis and Grading, Mar. 2010.

Arora, P. and Krishnan, A. "Fourier plane colorimetric sensing using broadband imaging of surface plasmons and application to biosensing," Dec. 16, 2015.

Huang, Fu Min et al. "Nanohole Array as a Lens," Jun. 2008.

Huang, Fu Min et al. "Focusing of Light by a Nano-Hole Array," Dec. 2006.

Jiang, Jing et al. "Plasmonic Nano-arrays for Ultrasensitive Bio-Sensing," published Aug. 28, 2018.

Schmid, P. "Segmentation of Digitized Dermatoscopic Images by Two-Dimensional Color Clustering," Feb. 1999.

Wisaeng, K and Sa-Ngiamvibool, W. "Improved fuzzy c-means clustering in the process of exudates detection using mathematical morphology," Mar. 7, 2017.

Wu, Li and Qu Xiaogang "Cancer Biomarker Detection: Recent Achievements and Challenges," Mar. 5, 2015.

Office Action dated May 3, 2024 for India patent application No. 202127023681.

Office Action and Search Report dated Nov. 20, 2023 for China patent application No. 201980090311.2.

Office Action and Search Report dated Jan. 3, 2024 for China patent application No. 201980090290.4.

\* cited by examiner

AUTOMATED METHOD OF IDENTIFYING A STRUCTURE

PCT/AU2018/050496 in the name of La Trobe University (the entire contents of which are herein incorporated by reference) discloses systems and methods of optical microscopy which provide enhanced image contrast through use of a sample holder having a plasmonic layer including a periodic array of sub-micron structures. The sample is placed on the sample holder adjacent the plasmonic layer. In use, the sample and sample holder are illuminated and an image of the sample is created. The inventors have observed that through interaction of the light with the sample and the plasmonic layer, a colour contrast is exhibited in the receive image. In particular, areas of the sample having different dielectric constant appear in the image with different colours. Intensity contrast is also achieved. In contrast to this, images obtained from conventional optical microscopy using a stained sample typically only exhibit an intensity contrast in a single colour which corresponds to the stain used. In the present disclosure reference to a nanoslide is reference to a sample holder in accordance with the teaching of PCT/AU2018/050496, or the Applicant's co-pending Australian patent application 2018904553, filed on 29 Nov. 2018, entitled "Microscopy method and system" and the International patent application claiming priority to AU2018904553 which was filed on the same day as present application, the contents of both being incorporated herein by reference for all purposes. Microscopy methods using such a sample holder are called or histoplasmonics or colour contrast microscopy herein, which is abbreviated to CCM.

FIELD OF THE DISCLOSURE

The present disclosure relates to the field of optical microscopy. In one form the disclosure provides systems and methods of automated analysis of digital images captured from an optical microscope.

BACKGROUND OF THE DISCLOSURE

Summary of the Disclosure

In a first aspect there is provided an automated method of identifying a structure in a sample. The method comprises, receiving at least one digital image of a sample wherein at least one localised structural property of the sample is visible in the image based on the colour of received light captured in the image. The method further includes processing the at least one image, based on the received colour information to selectively identify said structure. Most preferably the sample is a biological sample.

The method can include providing an output indicating the identification of the structure.

In the image received digital image, the localised structural property of the sample can be a localised refractive index. Accordingly a structure in the sample with a given refractive index appears as a corresponding colour or colour range in the image.

In some embodiments the method includes performing spectral analysis of at least a part of the received digital image.

In some embodiments the method can include any one or more of the following processing steps or sub-steps:
  Colour filtering the image to selectively process colour band of the received image;
  Determining a colour distribution or colour histogram of the received image;
  Performing a feature extraction method to identify one or more structures in the image;
  Processing the digital image with an image recognition system.
  Processing the digital image with an image recognition system to recognise one or more features in the image corresponding to one or more structures.

The image recognition system can be an artificial neural network or other suitable recognition system In some forms the features can be identified on the basis of one or more of: colour differentiation; and morphology differentiation. Preferably a combination of colour differentiation and morphology differentiation is used.

In embodiments that use more than one image of the sample the images can be images captured with any one or more of the following differences:

Different illumination characteristics (e.g. spectrum, polarisation), different magnification.

In a further aspect of the present invention there is provided a method of imaging a sample and automatically generating an indication of a presence of at least one structure in the sample. The method includes:

Providing a sample holder having a plasmonic layer including a periodic array of sub-micron structures.

Placing the sample on the sample holder adjacent the plasmonic layer.

Illuminating the sample and sample holder and capturing a colour digital image thereof; Performing a method of identifying a structure in the sample according to an embodiment of the first aspect of the present invention.

In some forms, a digital image used in the above aspects can be captured/generated using an embodiment of an aspect of any one of: any one of:
  PCT/AU2018/050496 or
  the applicant's co-pending Australian patent application 2018904553, filed on 29 Nov. 2018, entitled "Microscopy method and system" and the International patent application claiming priority to AU2018904553 which was filed on the same day as present application;
  the applicant's co-pending Australian patent application 2018904552, filed on 29 Nov. 2018, entitled "Method of identifying a structure" and the International patent application claiming priority to AU 2018904552 which was filed on the same day as present application, which is incorporated herein by reference for all purposes.

The methods herein can include generating an output indicating the presence of one or more features. The methods herein can be used to determine a state of at least one cell in a sample wherein determining a state of at least one cell is performed by identifying a structure based at least partially based on the colour of the at least one cell in the image.

This can be performed in accordance with the teaching of the applicant's co-pending Australian patent application 2018904550, filed on 29 Nov. 2018, entitled "Method of identifying a structure" and the International patent application claiming priority to AU 2018904550 which was filed on the same day as present application, both of which are incorporated herein by reference.

The method can include, determining a disease state of at least one cell.

In some embodiments the sample can contain a plurality of cells of the same type and the method can includes distinguishing at least one cell from cells of the same type based on based a colour contrast between the at least one cell and cells in the plurality of cells. In some embodiments the sample can contain a plurality of cells of different types and the method can includes distinguishing at least one cell of one or more types within the plurality of cells based a colour contrast between the at least one cell and cells in the plurality of cells. Preferably the method includes distinguishing at least one cell that is abnormal within the plurality of cells. In some cases the abnormal state can include cancer, benign abnormalities or infection. The method can include distinguishing at least one cell having in a benign abnormal state within the plurality of cells. For example the method can provide a method of distinguishing normal breast tissue from a benign abnormality/state, such as hyperplasia, or Ductal carcinoma in situ (DCIS) within a population containing a plurality of breast epithelial cells.

In embodiments of all aspects disclosed herein the structure can be, without limitation a cell, a cancer cell, part of a cancer cell, group of cancer cells, neoplastic cell, healthy cell, cell of a given type, indicator of cell state, parasite, group of cells, abnormal cell, infected cell, tissue of a given type.

BRIEF DESCRIPTION OF THE DRAWINGS

Illustrative embodiment of the present invention will be described by way of non-limiting example with reference to the accompanying drawings. The drawings filed with the present international application include colour images used in, and arising from use of embodiments of the present invention. The colour information forms part of the disclosure of the embodiments. Should black and white or grey-scale reproduction of the images occur, colour disclosure can be obtained from the originally filed documents. In the drawings.

DETAILED DESCRIPTION OF THE EMBODIMENTS

The present inventors have realised that the colour contrast exhibited in the images obtained using CCM can enhanced the ability to perform automated image analysis techniques on such images, e.g. to identify one or more structure within the sample, identify one or more properties of the sample in the image.

Figure 1:
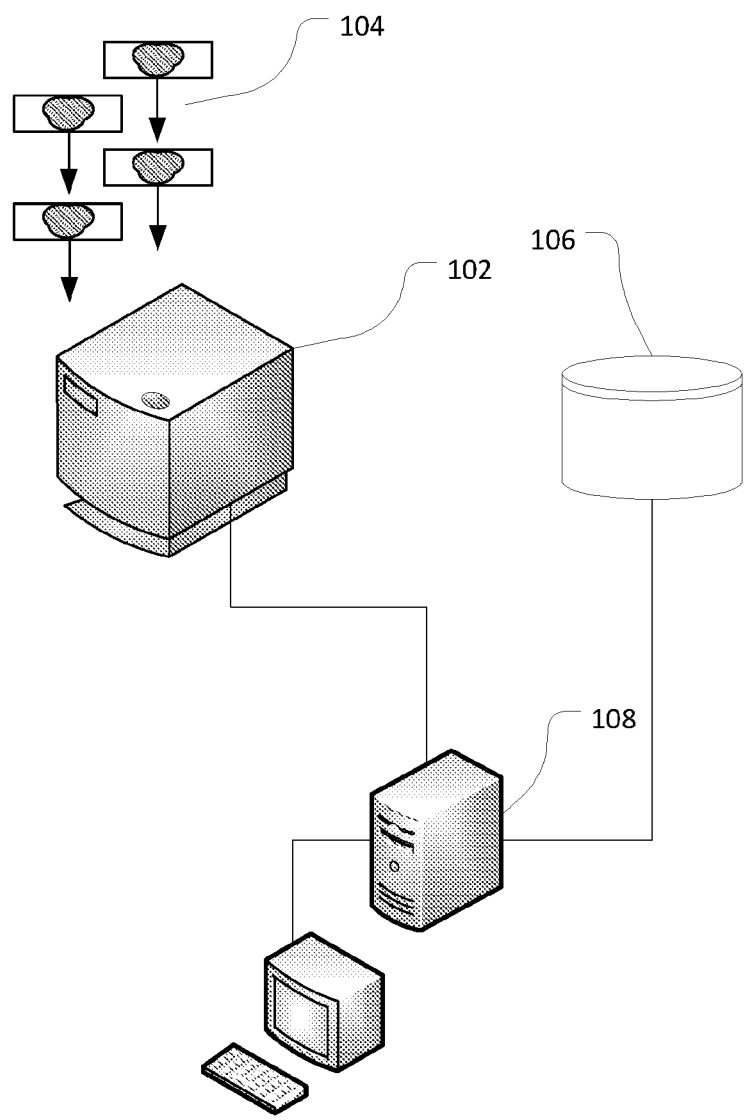
FIG. 1 is a schematic diagram of a system adapted to perform automated scanning of samples and analysis of images of according to an embodiment of the present invention.

FIG. 1 is an exemplary schematic representation of a system 100 configured to perform methods according to the present disclosure. In overview the system 100 includes an image capture sub-system and an image analysis sub-system. The image capture sub subsystem includes a slide scanner 102 adapted to capture images of a sample mounted on a sample holder 104. In other embodiments the slide scanner 102 can be replaced with a manual image capture means (e.g. digital camera) arranged to capture an image formed by an optical microscope. The sample holder 104 is a sample holder made in accordance with an aspect of PCT/AU2018/050496. The images captured in this fashion are then stored on a data storage system 106. The data storage system 106 can form part of (or be connected to) the slide scanner 102, a computing device 108 which controls the slide scanner 102, or be standalone data storage system. The image analysis subsystem comprises a computing device 108. The computing device is configured to control the operation of the slide scanner 102, receive images captured by the slide scanner, store these images, and perform analysis of them. A user terminal 110 is also provided to enable a user to interact with the computing device 108.

The present embodiment illustrates direct network connections between the elements of the system 100. The network connections may be wired or wireless, and may include a plurality of networks. In some embodiments two or more of the elements of the system 100 may not be collocated, and thus may be connected via the internet or other network adapted to enable remote communications between devices. Moreover two or more elements of the system may be combined into a single device or split into separate devices. For example the functions of the computer system 108 which operate to control the slide scanner 102 may be performed by an on-board control system computer of the slide scanner 102, or a dedicated control computer, whereas the image analysis functionality may be performed by a separate computer running suitable analysis software.

Figure 2:
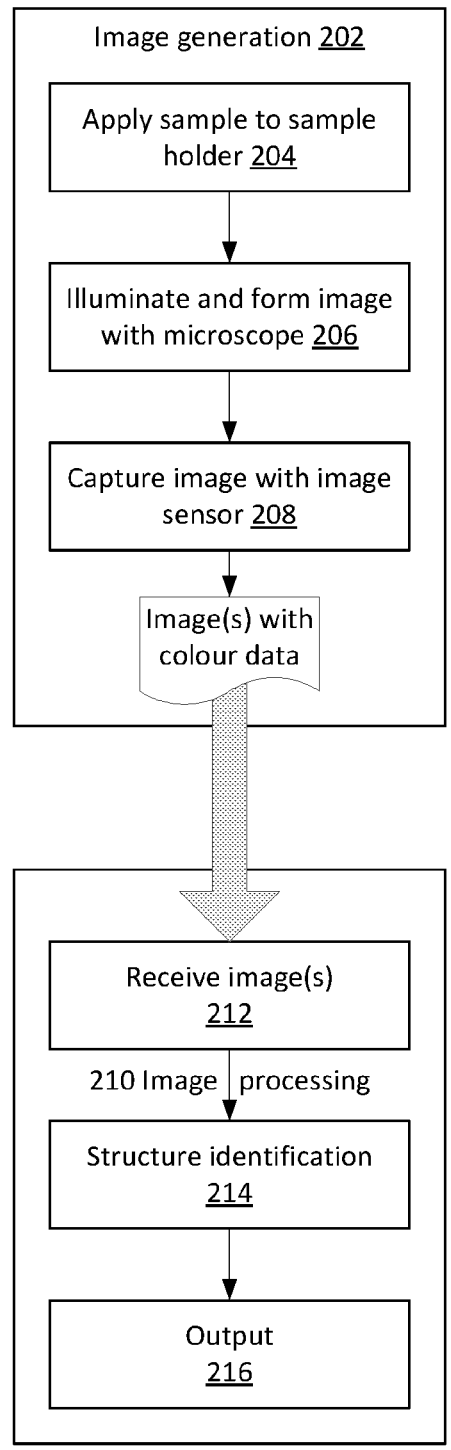
FIG. 2 illustrates a method performed by an embodiment of the present invention.
Figure 4A:
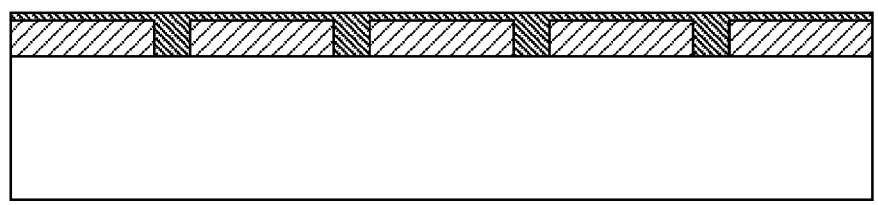
FIG. 4 illustrates details of an exemplary sample holder used in embodiments of the present disclosure. The present invention should not be considered to be limited to use of sample holders with the particular microstructure array illustrated in FIG. 4.
Figures 4B, 4C:
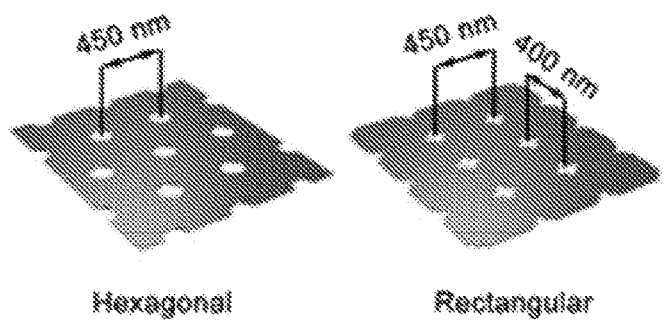

FIG. 2 shows the general scheme of operation of the system 100 in an embodiment of the present disclosure. The first phase 202 of the method 200 includes image generation. First 204 samples are prepared and placed on sample holders in accordance with an embodiment of PCT/AU2018/050496 in the name of La Trobe University. The sample holders each have a plasmonic layer including a periodic array of sub-micron structures, as set out in FIG. 4. FIG. 4a shows a cross section through a sample holder suitable for use in the present invention. The sample holder 104 includes a substrate 400, in which is deposited a plasmonic layer 402. FIGS. 4ba and 4c show the two types of plasmonic layer 402 with sub-micron arrays of that have been fabricated and may be used in an embodiment. The layers are each 150 nm thick silver films. FIG. 4b has sub-micron arrays in the form of circular shaped nanoapertures with a 450 nm period arranged in a hexagonal pattern. FIG. 4c has cross-shaped nanoapertures on a rectangular pattern. The cross-shaped nanoapertures have a 450 nm period in one direction (defined here as the 0° direction) and a 400 nm period in the orthogonal direction (defined as the 90° direction). These arrays have an SPP resonance mode in the 470-550 nm range, (which is within the visible region of the electromagnetic spectrum). To protect the surface of the plasmonic layer, a layer (10 nm±1 nm) of hydrogen silsesquioxane (HSQ), a glass-like material, is deposited after fabrication of the plasmonic layer. In other embodiments a metal oxide capping layer e.g. $SiO_2$ can be used in place of HSQ. After capping with HSQ, the sample holder has an upper surface similar to that of a conventional microscope slide on which a sample may be supported. It should be noted that the term upper surface and lower surface are not intended to reference a specific orientation of the sample holder either during sample preparation or use.

A sample, typically a slice of tissue, which need not be stained in the preferred embodiment of the present invention, is placed on the sample holder adjacent the plasmonic layer. The sample and sample holder are loaded into the slide scanner 102. The sample scanner illuminates (at step 206) the sample and sample holder and forms as image thereof (step 208). In essence the slide scanner 102 is a microscope that illuminates the sample holder and captures an image thereof. A suitable slide scanner could for example be a member of the Aperio slide scanners from Leica Biosystems or any other slide scanner capable of capturing colour images of a microscope slide or similar sample holder. The microscope can capture images in transmission or reflection mode.

The end result of the image generation phase 202 is one or more colour images of the sample, which can then be analysed in subsequent steps of the method. In an exemplary form the samples are imaged at high resolution (e.g., 240 nm per pixel).

The images may be of the whole sample holder, essentially a "whole-slide image". The image of the sample holder can be stored in a multi-resolution pyramid structure including a plurality of individual images providing multiple down-sampled versions of an original image. Each down sampled version is stored as a series of tiles, to facilitate rapid retrieval of sub-regions of the image. A typical whole-slide image may be approximately 200000×100000 pixels. In one form each image can be saved in RGB colour format with one byte per colour channel colour depth, although lesser or greater colour depth, or a different colour space may be used in some embodiments. The images are stored in the data storage system 106.

In the image processing phase 210 the image data of the whole slide or part of the slide are received (e.g. retrieved from data storage or received via a network connection, email etc.) and analysed to identify one or more structures (214) contained in the sample, and an output generated (216). The output can take a wide variety of forms. For example it may be, without limitation, one or more of the following:

Issuance of a notification message or alert; respect or after data reflecting the outcome of acid analysis;

Generation of an augmented image, (e.g. see FIG. 11) e.g. on which an identified structure or candidate feature which may be an identified structure is emphasised, rendered more visible or rendered identifiable to a user;

Generation of an image with metadata indicating the identification of a structure or one or more analysis steps performed thereon.

Figure 3:
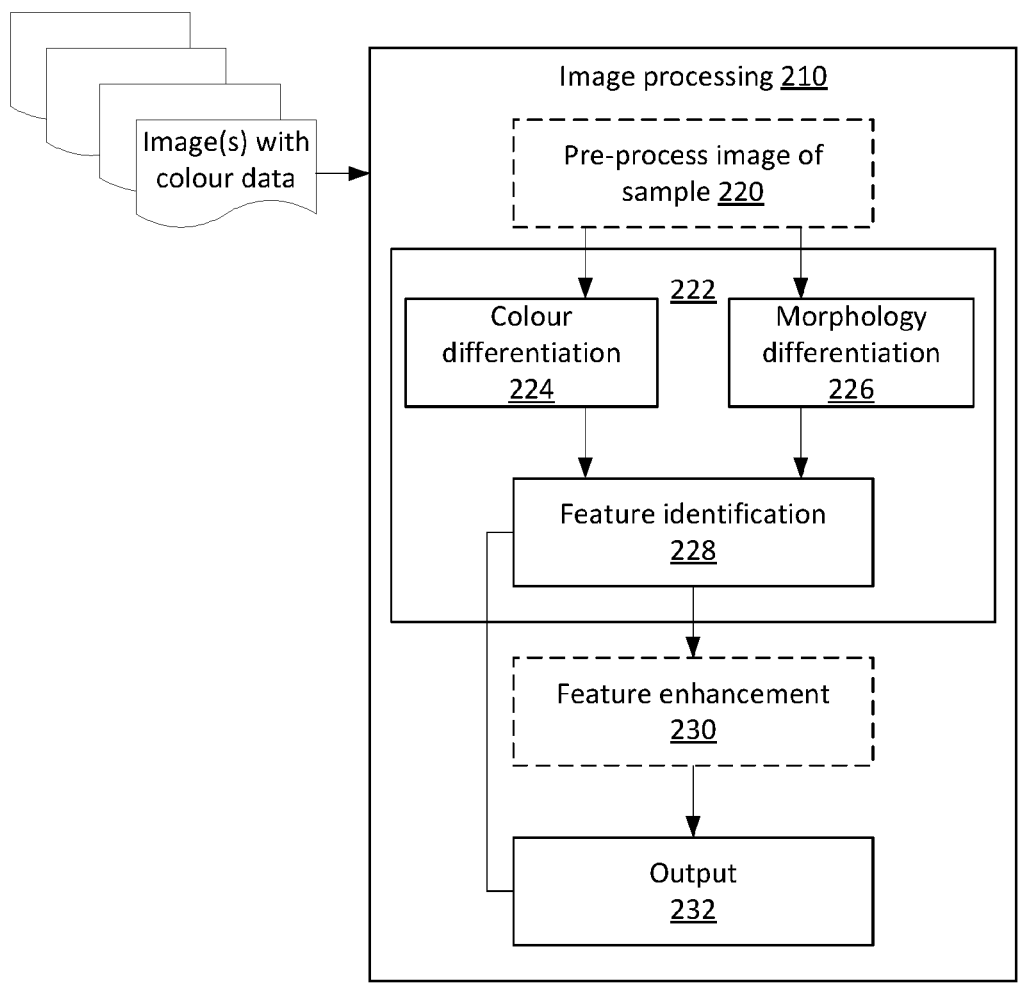
FIG. 3 illustrates details of an analysis method performed by an embodiment of the present invention.

FIG. 3 illustrates an example process for the image processing phase 210. The image processing phase 210 may include an optional initial pre-processing phase 220. The pre-processing phase 220 can include a range of processes that may be needed prior to feature analysis. For example this could include one or more of the following:

generation of a plurality of individual images from a single image, e.g. generating multiple down-sampled versions of an original image, subdivision of an image into a series of spatial tiles.

colour correction, balancing colour response of different colour planes in the image;

noise removal or noise equalisation.

It should be noted that the pre-processing steps may be omitted if the received image data is ready for image analysis without it.

Next, the image (or multiple images together) are processed to identify one or more features contained in the image. In a primary processing step colour-based image analysis is performed. In the present invention, the colour at a particular location in the image is representative of a local physical property of the sample. In particular by using a sample holder having a plasmonic layer including a periodic array of sub-micron structures a colour contrast is exhibited in the received image. In particular, areas of the sample having different a dielectric constant appear in the image with different colours.

The underlying mechanism for the extraordinary optical contrast in the images is the resonant interaction of light with the collective oscillations of free electrons at a metal surface in the plasmonic layer of the sample holder, known as Surface Plasmon Polaritons (SPPs). The spectral change in transmitted light through an array of sub-wavelength apertures in contact with a dielectric specimen is a function of the wavelength shift, $\Delta\lambda$ of the SPP resonant modes $\lambda^\theta_{SPP}$, where superscript $\theta$ denotes the incident polarisation angle (the symbol is removed for unpolarised light) and the subscript indicates whether the dielectric constant is for the sample (d=s) or for air (d=a). The SPP modes are characterised by peaks in the transmission spectra, the corresponding wavelength shift relative to air when a sample of thickness t is placed on top of the nanoapertures is given by:

$$\Delta\lambda \approx (\lambda^\theta_{SPP,s} - \lambda^\theta_{SPP,a})(1-\exp(-2t/l_d)), \quad (1)$$

where $l_d \sim 2\sqrt{\varepsilon_d}$ is the characteristic decay length of the SPP electromagnetic field, which is itself a function of $\varepsilon_d$, the dielectric constant of the sample. It should be noted however that in the preferred embodiments the sample is significantly thicker than the characteristic decay length of the sample. As the film thickness increases, the transmission SPP resonance peak is increasingly red-shifted until it equals $\lambda^\theta_{SPP}$, after which no more colour change occurs. It follows that, when using a standard transmission bright-field microscope, or reflection microscope, a spatially resolved distribution of colours will result that relates directly to changes in the local dielectric constant in the sample. With the local dielectric constant encoded in the optical spectrum, a remarkable chromatic contrast effect is produced. This means that any structure within optically transparent samples, which previously was difficult to detect due to a lack of contrast, is detectable in the visible-light image, by virtue of the colour contrast captured in the images.

Next in step 222 an image (or two or more images) is analysed to identify features in the image (or two or more images) that are representative of one or more structures of interest in the sample. A structure of interest can, for example include, a cell, group of cells, part of a cell, interstitial space between cells, void in a cell, the morphology of any of the above. In some embodiments the method can include any one or more of the following processing steps or sub-steps:

Colour filtering the image to selectively process (e.g. perform feature differentiation) on one or more colour bands of the received image, or an image generated from one or more colour bands;

Determining a colour distribution or colour histogram of the received image;

Performing a feature extraction method to identify one or more structures in the image;

Processing the digital image with an image recognition system.

The analysis in step 222 can be grouped into two general types of processes:

Colour differentiation (224), which encompasses differentiation methods based on the localised colour of the image of the sample, relative colour of more than two locations in the image, overall colour/spectral content of the image or portion thereof. Colour differentiation can be based on a CIE plot which mimics sensitivity of the human eye. In some embodiments a spectral 'fingerprint' can be generated for an image or portion thereof. The spectral fingerprint can enable either a coarse analysis based on e.g. where the spectral fingerprint in the form of an RGB ratio is compared to values in a look up table to determine if a sample is 'healthy' or not. Alternatively a more detailed spectral fingerprint can be compared against a higher resolution spectrum e.g. collected using a spectrometer. As will be appreciated in analysing any one image (or set of two or more images) multiple colour differentiation techniques can be used. An exemplary colour-based analysis method 222 is described below in relation to FIG. 5.

Morphology differentiation (226), which uses the shape characteristics of one or more structures in an image to identify the structure. In some the forms morphology process can include contour analysis to identify the shape of a given structure(s) in an image. Further examples of morphology differentiation methods that could be applied in an embodiment is described in Peng H, Zhou X, Li F, Xia X, Wong ST. INTEGRATING MULTI-SCALE BLOB/CURVILINEAR DETECTOR TECHNIQUES AND MULTI-LEVEL SETS FOR AUTOMATED SEGMENTATION OF STEM CELL IMAGES. Proc IEEE Int Symp Biomed Imaging. 2009; 2009:1362-1365. Other morphology differentiation methods could be used. In some forms morphology differentiation can be performed on a colour filtered representation of the image (e.g. performed on one colour plane in the image) or on a pre-processed image that combines multiple colour planes (e.g. a luminance image) derived from the captured images.

Figures 5, 6:
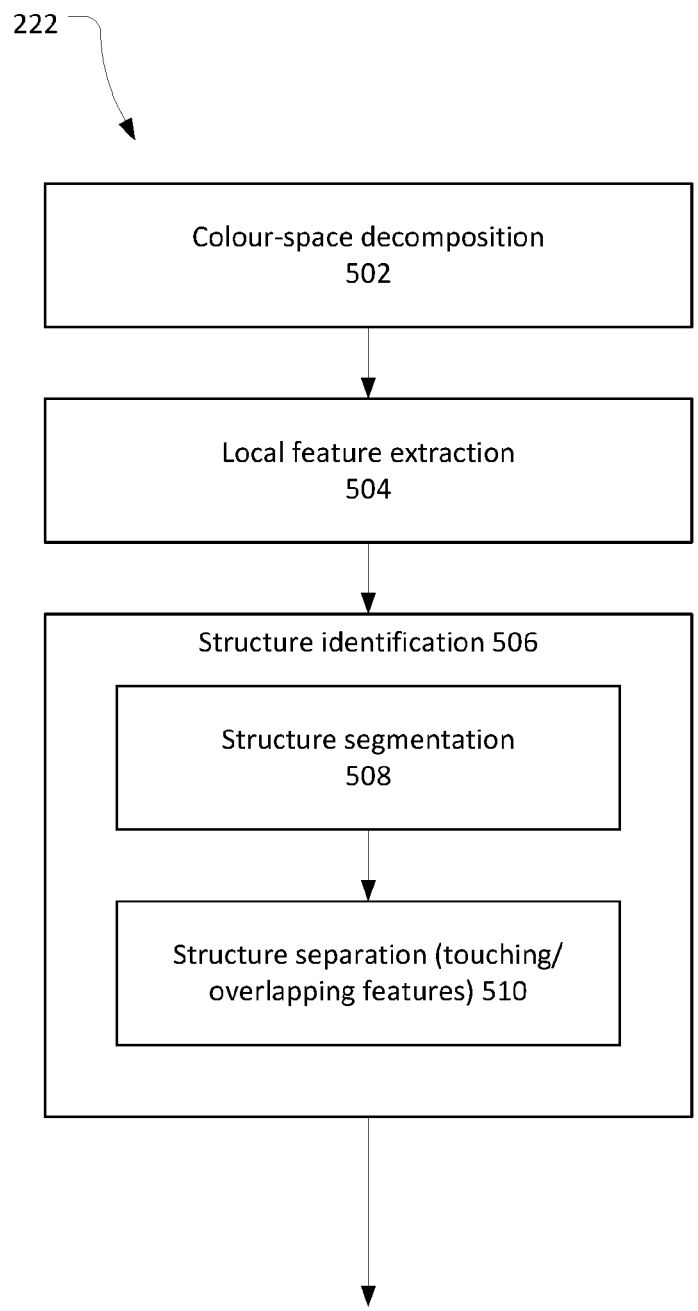
FIG. 5 is a flowchart showing steps in a colour-based structure identification method usable in an embodiment of the present invention.
FIG. 6 illustrates an example range of HSL colour space values corresponding to cancer positivity in PyMT models using nanoslide.

An exemplary colour-based differentiation process 222 is shown in FIG. 5. The method 222 begins by choosing a colour space in which to perform processing. In the present example a HSL colour space (Hue, Saturation, Lightness) is used. As such each pixel in the received image(s) are represented by value corresponding to each parameter. Conversion between the colour space of the received image(s) and the chosen colour space may be needed. Next in step 504 local feature extraction is performed. This process involves analysis of the received image(s) based on colour to identify pixels that may correspond to the structure of interest. The correlation between the structure of interest and its colour in the received image(s) may be known, or determined from preliminary analysis of the image(s). For example in experiments performed by the inventors, colour correlations between structures of interest (cancer cell nuclei, in samples from a PyMT model) were determined by inspection of a plurality of images by experts. In particular, to establish the HSL range for cancer cell identification using the nanoslide, images of slides were compared to a ground truth standard for the PyMT model. Adjacent breast tissue sections were independently classified by examination of the morphology by a breast cancer expert following a protocols similar to that established in the literature for automated segmentation of Ki67 images on the basis of hue (e.g. Shi et al., Scientific Reports, 2016). The same process was performed on corresponding (adjacent sections) for Ki67 images to enable comparison with the present methodology.

Both methods generally follow the process of Shi, P. et al. Automated Ki-67 Quantification of Immunohistochemical Staining Image of Human Nasopharyngeal Carcinoma Xenografts. Scientific Reports 6, 32127, doi:10.1038/srep32127 (2016), the contents of which are incorporated herein by reference.

For both the nanoslide images and Ki67 images the mean RGB space and HSL space values for the cancer cells were determined from the ground truth standard. Cancer cells when imaged on the nanoslide manifest themselves as generally blue in hue, whereas, Ki-67 positive nuclei manifest themselves as brown hue in images of breast tissues.

The mean RGB and HSL channel values for positive cancer cells in Ki67 and nanoslide are summarised in Table 1 below. The RGB values for Ki67 positivity determined by the inventors are close to the published values from (Shi et al., Scientific Reports, 2016).

TABLE 1

| Values | Mean RGB space values | | | Mean HSL space values | | |
| --- | --- | --- | --- | --- | --- | --- |
| | R | G | B | H | S | L |
| Ki67 (brown) | 123 | 51 | 7 | 23 | 89 | 26 |
| Nanoslide (blue) | 23 | 69 | 86 | 196 | 58 | 21 |

Based on the variability of the colour change associated with cell positivity in nanoslide and Ki67 a ±15% threshold centred around the mean HSL colour space values (in each of H, S and L) was used for segmentation of positive cancer cells—that is, within this range cells were considered to be 'positive' for cancer. An example range of HSL colour space values corresponding to cancer positivity using nanoslide is shown in FIG. 6.

In the local feature extraction step 504 pixels of the image(s) having HSL values corresponding with cancer positivity are selected. In the present example using the nanoslide only a single colour range is considered, but other embodiments may perform multiple segmentations based on different colour ranges to attempt to identify respective structures in the image(s). Pixels having colour values in the selected range are further analysed to identify groups or subsets of pixels that may represent the structure of interest (e.g. nucleus of a cancer cell). The subsequent analysis can include analyzing the pixels to identify correlation between a pixel and at least one neighbouring pixel. In some examples, the mean intensity and standard deviation at a pixel site can be calculated based on a 3×3 group of pixels centred on the pixel, and can be used as a measure of signal strength and local variance on signal strength in the neighbourhood of the pixel site. The skewness and kurtosis of pixel and its surrounding 3×3 neighbourhood of pixels can be calculated. The skewness measures symmetry of local intensity and whether the intensity is more peaked or flat than a normal distribution. These measures of local pixel correlation can be used to cluster similar pixels or separate dis-similar pixels into clusters (representing structures of interest) in step 508. Grouping can be performed using kmeans clustering or other suitable techniques, as part of a structure identification step 506. It may be necessary to more accurately define the boundary of a structure of interest. In step 510, clusters representing touching or overlapping features can be separated into individual clusters. This can be performed, e.g. using the watershed method.

In step 228 the output of the differentiation processes are used to make a decision on the presence or absence of one or more features in the image which indicate the presence or absence of a structure in the sample.

In some embodiments a combination of colour differentiation in addition to sample morphology differentiation enables more accurate identification of a structure. For example a spatial correlation between the output form colour differentiation and morphology differentiation could be used to distinguish between features that are indistinguishable by one process alone.

The image recognition system can be an artificial neural network. The image recognition system can be trained on a suitable training set of images containing known structures. Saha, M. et al., An exemplary image recognition method and system that could be used in embodiments of the present invention is described in "An Advanced Deep Learning Approach for Ki-67 Stained Hotspot Detection and Proliferation Rate Scoring for Prognostic Evaluation of Breast Cancer. Scientific Reports; 7: 3213 DOI:10.1038/s41598-017-03405-5, (2017) describes a deep learning methodology using an ANN system to detect breast cancer cells for Ki67 stained samples. Such a methodology could be applied to images taken with a nanoslide to identify similar structures as taught herein.

In the event that one or more features are identified in step 228 the one or more images, an output is generated at 232. The output can take many forms. The output can take a wide variety of forms. For example it may be, without limitation, one or more of the following:

Issuance of a notification message or alert;
Generation of an augmented image (in step 230), e.g. on which an identified structure or candidate feature which may be an identified structure is enhanced e.g. it can be emphasised, rendered more visible or rendered identifiable to a user;
Generation of an image with metadata indicating the identification of a structure or one or more analysis steps performed thereon.

Feature enhancement can include showing the boundary of the structure or structures which have been identified in the image(s) in an augmented image. The boundary can include drawing a bounding box or other outline around the identified features. This can be of use to a user of the system to rapidly enable identification and human investigation and verification of the presence or absence of the structure.

Methods disclosed herein can be used in an implementation an embodiment of an aspect of the applicant's co-pending Australian patent application 2018904550, filed on 29 Nov. 2018, entitled "Method of identifying a structure" and the International patent application claiming priority to AU 2018904550 which was filed on the same day as present application.

EXAMPLE

To illustrate the usefulness of the present method, automated image processing is performed using nanoslide images on the basis of the HSL (hue, saturation, lightness) of the image pixels. The results were compared to those obtained from analysis of samples stained using proliferative markers (Ki67) and illustrate the technique can distinguish a structure, which in this example is distinguishing neoplastic cells, as compared to normal breast epithelium.

In the present example sample holders having a plasmonic layer with a periodic array of sub-micron structures (e.g. circular holes) were fabricated using displacement Talbot lithography to produce devices on the scale of whole microscope slides (e.g. 75 mm×25 mm). The nanoslides were used in conventional brightfield imaging of samples and histological tissue sections of corresponding samples were scored by two reference pathologists. The properties of the brightfield images were analysed based on the measured hue, saturation, and lightness in the image.

Figure 7A:
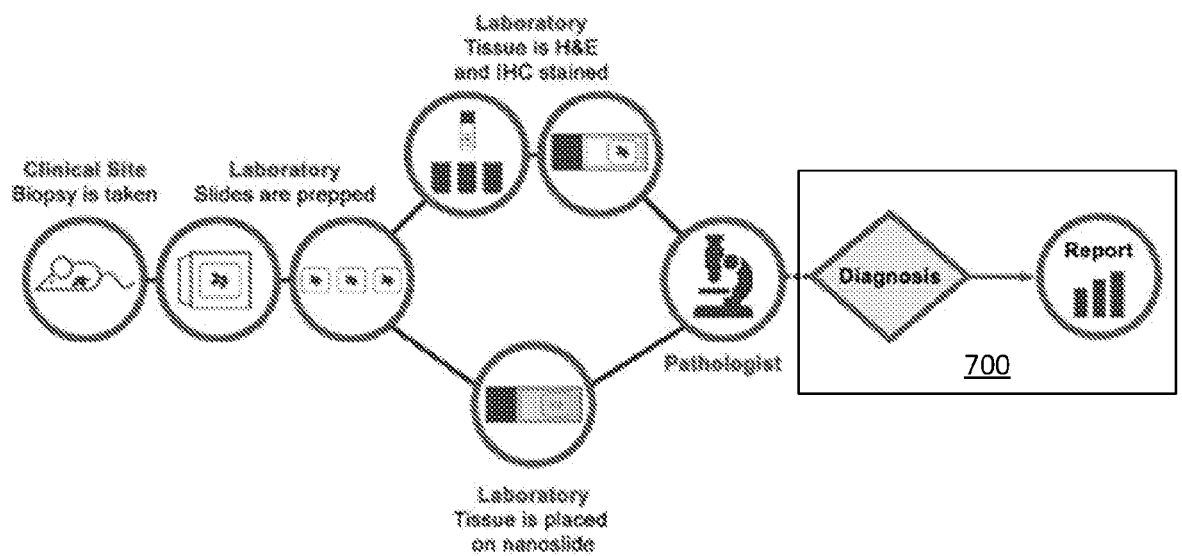
FIGS. 7a and 7b illustrate schematically the pathology workflow for small-animal, MMTV-PyMT mouse model study.
Figure 7B:
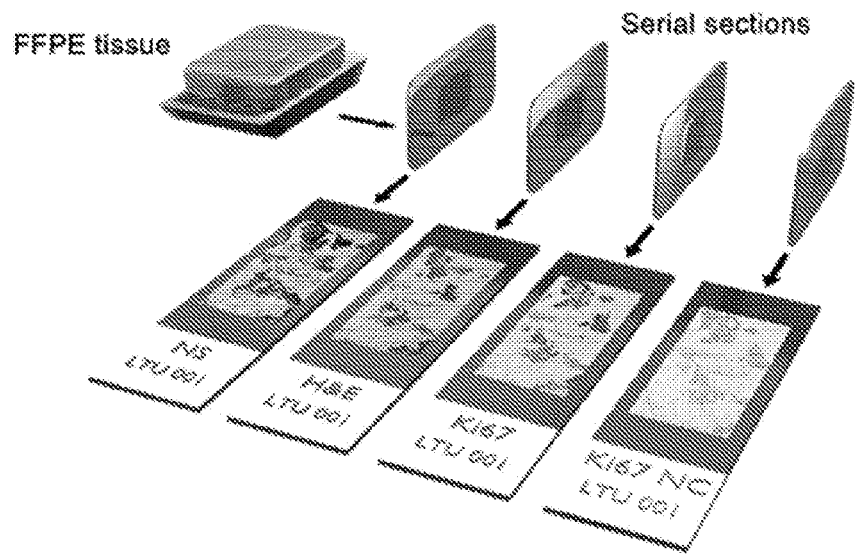

FIGS. 7*a* and 7*b* together illustrate, schematically the pathology workflow for small-animal, MMTV-PyMT mouse model study including, showing how serial sections were taken in order for a direct comparison of nanoslide, H&E, and Ki67.

In the study the images made use of the MMTV-PyMT model of spontaneous breast tumorigenesis, where mice develop pre-invasive and invasive neoplasms within 50 days of age. Pre-invasive and invasive neoplasms have previously been shown to be distinguishable from benign epithelial cells using IHC staining for the proliferative marker Ki67. In total 24 mice were used for this study. The workflow for the study design is shown in FIGS. 7*a* and 7*b*. For each slice of tissue sectioned and placed on a nanoslide the neighbouring section was H&E stained (for use as the ground truth analysis by expert human analysis) whilst the next two sections were treated with IHC staining (one section with the proliferative marker and the other with control IgG.

For the nanoslide and Ki67 stained samples automated image analysis as set out above was performed in step 700 to identify the presence or absence of neoplastic cells.

Figure 8:
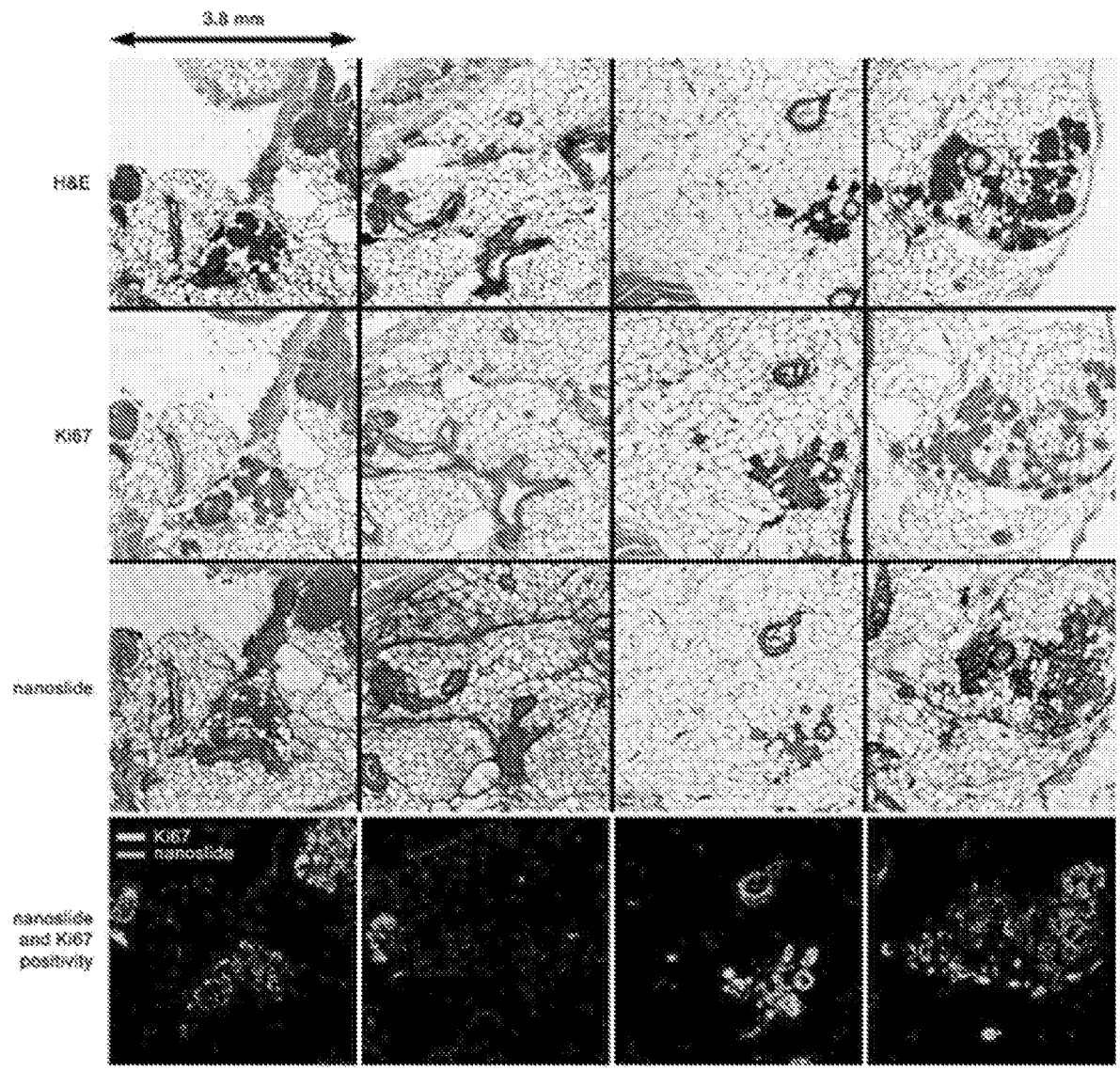
FIG. 8 shows large field-of-view (3.8 mm) sections of corresponding slices of H&E, Ki67, and nanoslide images (top to bottom), with the bottom row showing portions of the images identified by an automated image analysis method based on their respective HSL colour space values to be positive for neoplastic cells. Regions with HSL values consistent with neoplastic MMTV-PyMT breast cancer cells are shown in light blue (nanoslide) and bright green (Ki67).

FIG. 8 shows large field-of-view (3.8 mm) sections of corresponding slices of H&E, Ki67, and nanoslide images (top to bottom); each slice is 4 μm thick (>>Id for the nanoslide). These sections cover a range of different tissues types (e.g. lymph nodes, collagen, muscle tissue, ligament etc.) and also include regions of pre-invasive and neoplastic breast tissue. Using the ground truth pathology assessment and the comparative Ki67 staining the HSL values associated with cancer cells were identified for nanoslide. A total of 64 regions were examined across the cohort of 24 mice. In the bottom row of FIG. 8 the regions with HSL values consistent with neoplastic MMTV-PyMT breast cancer cells are shown in light blue (nanoslide) and bright green (Ki67).

Figure 9:
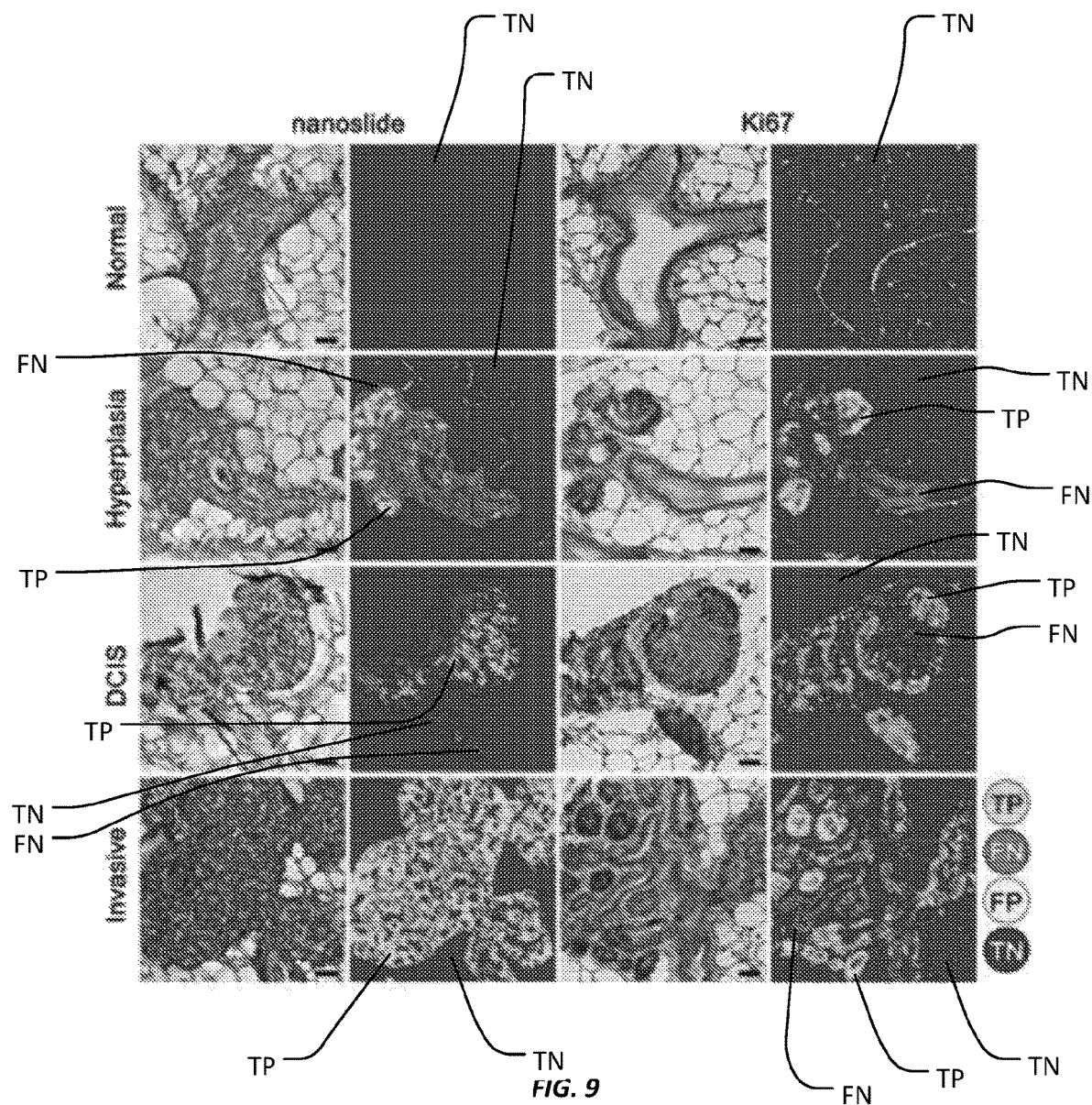
FIG. 9 shows an example output indicating the identification of a structure the automated segmentation of small-animal data based on HSL colour space and assessment by a breast-cancer pathologist.

Following established protocols tissue (as identified by the automated image analysis of the nanoslide images) was classified as True Positive (TP), True Negative (TN), False Positive (FP), and False Negative (FN) as compared to human analysis. In the human classification, pathology annotations, when a cancer containing region has been identified, high-resolution H&E stained slides were used to identify the stage of the cancer and the margins. A morphological assessment of the tissues was conducted by an expert human breast and murine mammary gland pathologist (O'Toole) and breast cancer researcher (Parker) and formed the 'ground truth' for the analysis. The second piece of information came from the image pixel HSL colour space values which were compared against the reference values from the training data (as set out for the nanoslide in FIG. 6). Regions containing normal, hyperplasia, DCIS (ductal carcinoma in situ), and invasive neoplastic breast tissue were independently analysed for both nanoslide and Ki67 staining. Some example images of each type of region and resulting tissue classification are shown in FIG. 9. Classification was applied according to the following descriptions.

| Classification | Description of classification method for Ki67 and Nanoslide |
|---|---|
| True Positive (TP) | TP was assigned when the HSL colour space values were consistent with cancer cells established by 'training' the segmentation algorithm. This 'training' was conducted based on the identification and correlation of cancerous tissue in Ki67 and nanoslide images by the expert pathologist with reference to the H&E slides (e.g. Shi et al, Scientific Reports, 2016). To be classified as TP also required that the identified region was within the area manually identified as containing cancer cells by the expert pathologists. |
| True Negative (TN) | TN was assigned when the HSL colour space values were consistent with one of the sub-types of non-cancerous tissues (e.g. adipose tissue, collagen, lymph nodes, blood vessels etc.). To be classified as TN also required that the identified region was outside of the area manually identified as containing cancerous tissue by the expert pathologists. |
| False Positive (FP) | FP was assigned when the HSL colour space values were consistent with cancer cells but the identified region was outside of the area manually identified as containing cancer cells by the expert pathologists. |
| False Negative (FN) | FN was assigned when the HSL colour space values were not consistent with either cancer cells or with non-cancerous tissue and when the identified region was within the area manually identified as containing cancer cells by the expert pathologists. |

FIG. 9 illustrates high-resolution images taken across 24 MMTV-PyMT mice were sub-categorised (as set out under the heading "Pathology assessment" below) into four different stages (normal, hyperplasia, DCIS, and invasive) for both nanoslide (1st column) and Ki67 (4th column) based on annotations from the pathologist. The automated analysis based on HSL colour space values for each image were compared against ground truth annotations by a pathologist, the evaluation results are classified in terms of TP (green), FN (red), FP (yellow), and TN (blue) regions. The images (1st and 3rd columns) are presented as they appear under the microscope. Neoplastic cells in pre-invasive and invasive neoplastic tissues were easily distinguished from surrounding cells in the same tissue and benign tissues via a colorimetric differential interaction as a result of either staining (Ki67—brown colour) or as a result of variations in the local dielectric constant (nanoslide—blue/purple colour). As seen, adipose and other types of non-cancerous tissue observed across the slides have a characteristically different colour (HSL) on both the nanoslide and Ki67, supporting this association. As can be seen the normal cells on the nanoslide appear to be almost uniformly categorised as TN. The invasive cells image on the nanoslide image was categorised as a large majority of TP regions surrounded by TN areas, showing accurate categorisation by the automated image analysis. The DCIS and Hyperplasia images include a region of majority TP towards the centre of the neoplastic regions surrounded by areas of mixed FN, TP, TN regions.

Figure 10A:
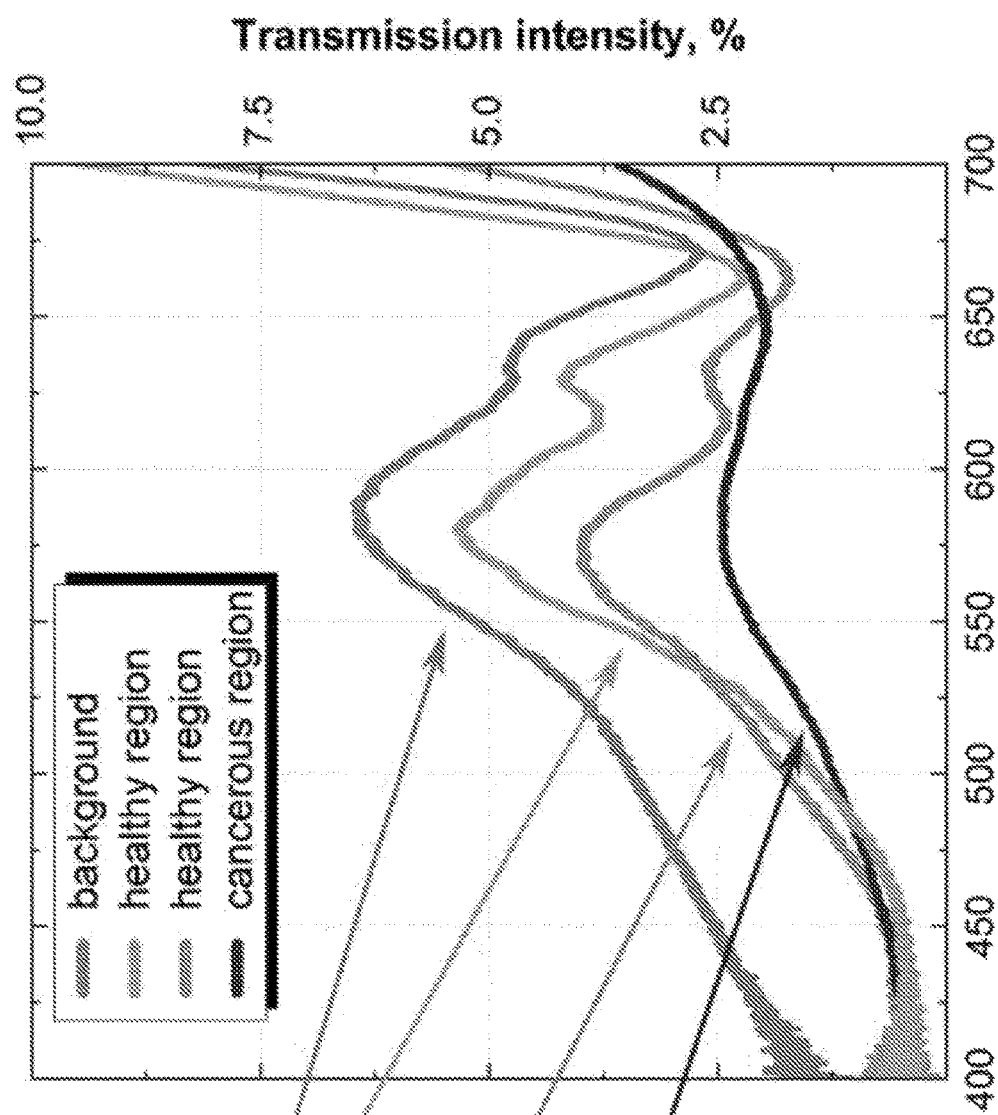
FIG. 10a shows the spectral characteristics of healthy and cancerous tissue.
Figure 10A:
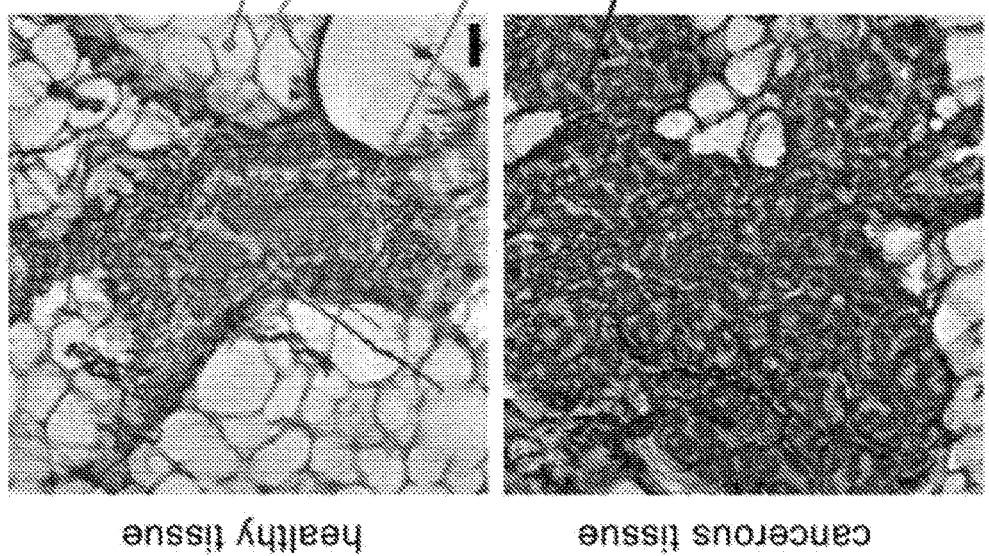

The methods disclosed herein use utilise the differences in the spectral output between structures to identify those structures. FIG. 10A, illustrates the received colour spectrum of benign and neoplastic breast tissue which giving rise to colour contrast in nanoslide images. On the basis of the 24 MMTV-PyMT mice studies the spectral output of cancer cells appears to be distinct from other types of non-cancerous tissue providing a novel mechanism for performing digital pathology. To further validate the results against published standards the inventors used an established scoring matrix for discriminating 'normal', hyperplasia, DCIS and invasive lesions. As revealed in results presented in FIG. 10b, both approaches (nanoslide and Ki67) identify a similar percentage of neoplastic cells in a randomised preclinical study. DCIS comprises lesions which are heterogeneous with highly variable morphology; whereas at the extremes of normal and invasive, breast cancer is easy to discern, DCIS is subtle and consequently suffers from misdiagnosis based on H&E alone particularly at large fields-of-view.

Figure 10B:
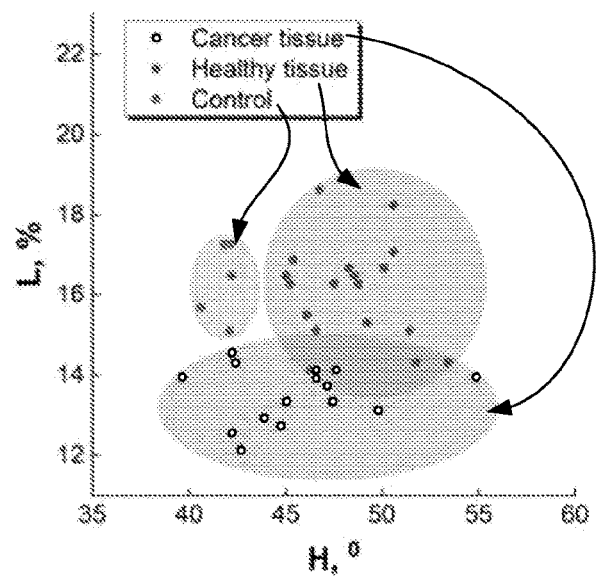
FIG. 10b, shows the output of regions evaluated by an expert breast cancer pathologist plotted as a function of luminosity (L) versus hue (H).

FIG. 10b shows how the automated method described herein using a nanoslide sample holder discriminates between structures in a sample. In this case it has been shown that 'healthy' and invasive cancer tissue can be identified based in the hue (H,°) and luminosity (L, %) of the images. Note that the 'healthy' tissue sections are taken from MMTV-PyMT mice, 90% of which will eventually develop pre-invasive and invasive neoplasms, hence a small amount of overlap may be expected when comparing to invasive cancer regions. The difference between normal and cancer mammary tissue is further validated by the clear discrimination between normal/benign tissue in wildtype animals and neoplastic tissue.

Figure 10C:
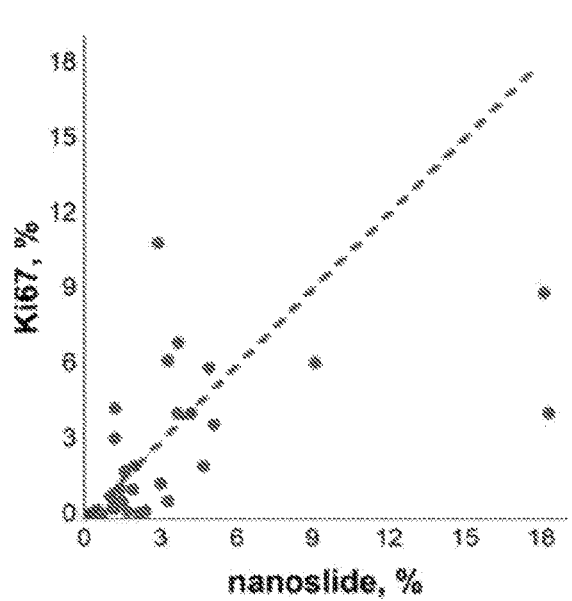
FIG. 10c, shows the percentage of cells positively identified as being cancerous on the basis of HSL colour space values.
Figure 10D:
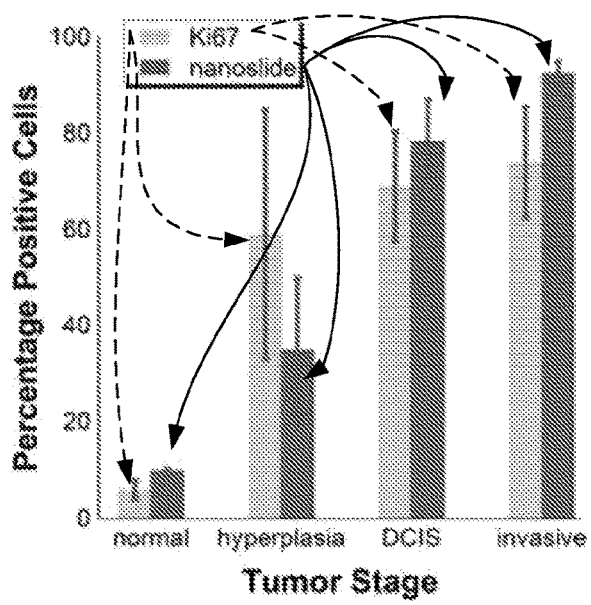
FIG. 10d, shows pathology scoring of Ki67 and nanoslide images for data collected from 24 mice, the percentage of cells identified as cancerous is indicative of the tumour stage.
Figure 10E:
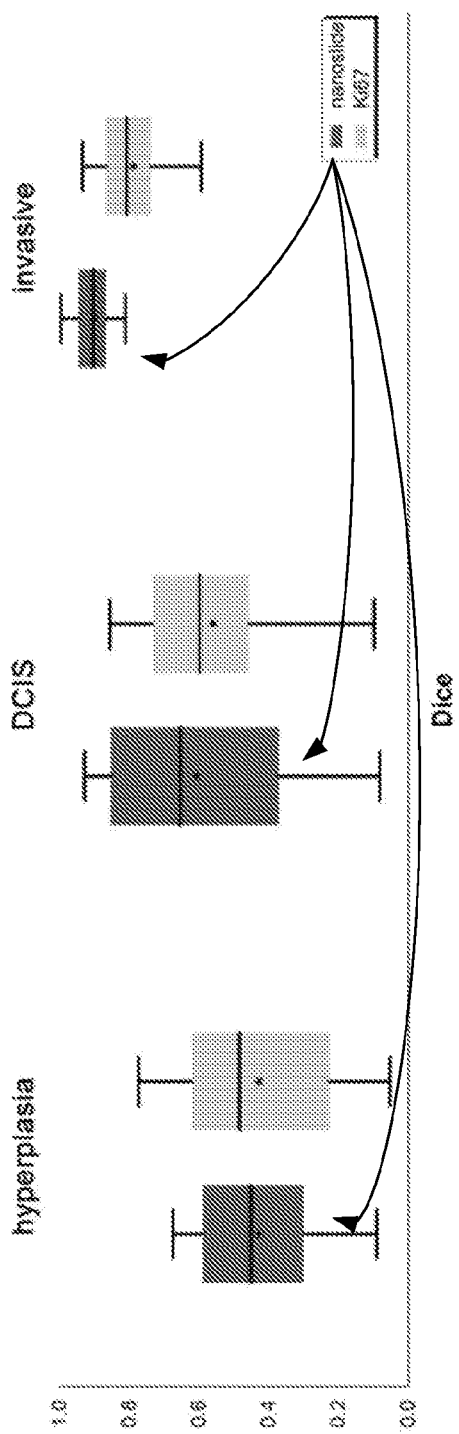
FIG. 10e, shows the agreement of Dice coefficients for nanoslide and Ki67 for three different classes of neoplastic region.

To test the concordance of Ki67 and nanoslide we compared the percentage (by area) of tissue identified by the two pathologists as containing neoplastic cells according to the image pixel HSL colour space values; the results are summarised in FIG. 10c. For the regions examined (N=30) nanoslide and Ki67 exhibit highly positively correlated performance metrics. The Pearson correlation coefficient, r, and corresponding p-value for the Ki67 and nanoslide results confirm a positive correlation: $r(28)=0.62$, $p<0.001$. Of the cancer bearing tissues examined none had both non-zero Ki67 positivity and zero nanoslide positivity and only two had non-zero nanoslide positivity but zero Ki67 positivity. FIG. 10d, shows pathology scoring of Ki67 and nanoslide images for data collected from 24 mice, the percentage of cells identified as cancerous is indicative of the tumour stage. The positive correlation between Ki67 and nanoslide supports the breast cancer pathologists manual scoring (FIG. 10d) and concurs with FIG. 10e, that shows the Sorensen-Dice coefficient (DSC) coefficients for nanoslide and Ki67 for three different classes of neoplastic region. The DSC is defined as:

$$DSC = 2TP/(2TP+FP+FN)$$

Calculated for both nanoslide and Ki67 (FIG. 10e) based on the analysis of 64 high-resolution (200×magnification) images from both Ki67 and nanoslide data.

Figure 11A:
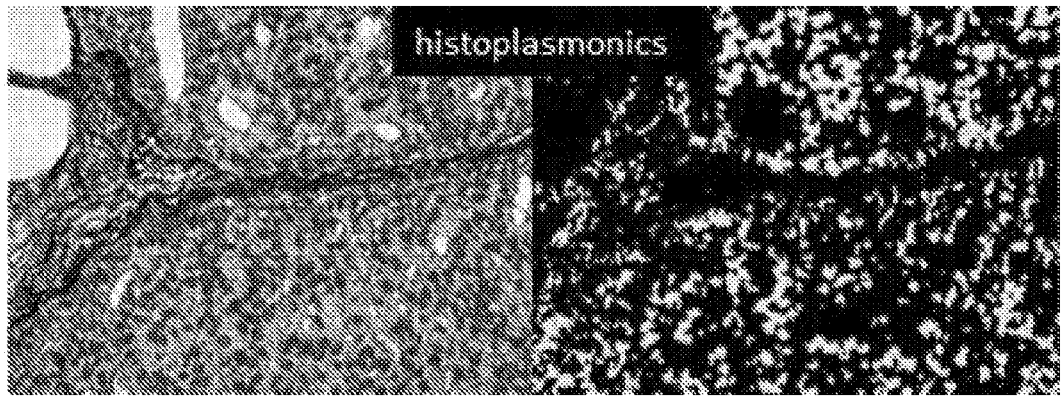
FIG. 11 shows an example implementation of an embodiment of the present invention used to detect a structure in human cells. In this case the structure are cancerous cells.

FIG. 11 shows an example implementation of an embodiment of the present invention used to detect a structure in human cells. In this case the structure are cancerous cells. FIG. 11a shows the image illustrating DCIS in breast tissue imaged with CCM, whereas 11 b shows the image illustrating DCIS in breast tissue imaged with IHC staining. In each image the right hand panel shows a segmented image that identifies portions of each captured image having a colour within 15% of the mean colour of cancer for the sample (see FIG. 6 for the CCM colour range, and table 1). As can be easily observed significant numbers of differentiated cells can be observed in the CCM image.

Figure 11B:
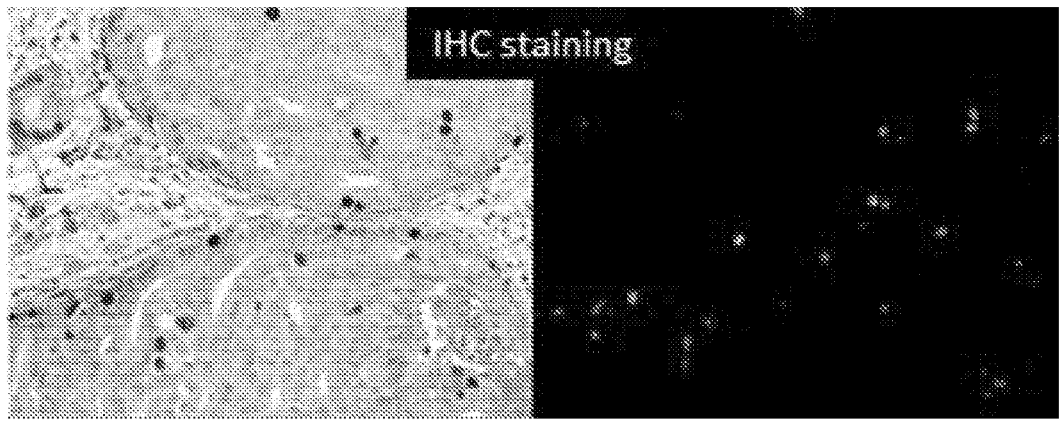

This compares favourably in to IHC staining based on proliferative markers (FIG. 18b) which positively identifies few cancer cells. The human tissue sample was imaged on a nanoslide (FIG. 11a left) and by Ki67 IHC staining (FIG. 11b left). The images were processed using the automated image processing method described herein, in the same way as the mouse samples in the previous example. FIG. 11a right illustrates the segmented nanoslide image, illustrating those portions of the image determined to represent the structure of interest, namely breast cancer cells. In FIG. 11b (right panel) each blue "blob" represents a pixel cluster determined by the image processing to represent a cancer cell imaged on the Ki67 stained slide.

Pathology Assessment

In the example to confirm the timing of spontaneous development of mammary gland tumours in the C57 Bl/6 MMTV-PyMT model, mammary glands of C57 Bl/6 MMTV-PyMT mice at different stages were taken and morphologically evaluated by H&E and Ki67 by an expert human breast and murine mammary gland pathologist (O'Toole) and breast cancer researcher (Parker). Nanoslide samples were randomized and independently scored and then compared post-analysis to the results of Ki67 and nanoslide. The benchmark for the pathology assessment was a trained pathologist analyzing the H&E stained tissue sections at high-resolution and without any time constraints. As this was a control study the cancer stage for the mice was already known by the pathologist. In addition, the pathologist could refer back to the IHC staining to confirm that no neoplastic tissue regions were missed during the assessment. When looking at a tumor region or duct containing cancer at high resolution the pathologist counts the number of cancer cells.

Once this has been done for all samples the pathologist then compared the number of individual positive cells (as determined by a colour change—'brown' for Ki67 and 'green' for nanoslide) using either Ki67 or nanoslide and divided this number by the total number of cancer cells identified from pathological assessment of the H&E images to arrive at the final figure for "percentage positive cells". This analysis was conducted on 24 cancer containing regions across the 24 mice used in this study. Based on the knowledge of the cancer stage the results could be classified into 4 stages: 'normal', 'hyperplasia', DCIS', and 'invasive'. The mean value of the percentage of positive cancer cells as determined by the pathologist was calculated within each category, it is this mean value, averaged between the two independent sets of scores, which is represented by the height of the bars in the bar chart. The range (e.g. minimum and maximum percentages) over the different samples used to generate the error bars shown in FIG. 10d. The scoring matrix for discriminating normal, DCIS, and invasive lesions is shown in the following table

|  | Normal | DCIS | Invasive |
| --- | --- | --- | --- |
| Appearance of lumen | Empty Lumen | Filled Lumen | No Lumen |
| Epithelial Ki67 positivity (95% confidence interval) | 0-28% | 44-66% | 48-96% |

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of imaging a sample and automatically identifying a presence of a structure in the sample, the method including:
   providing a sample holder having a plasmonic layer including a periodic array of sub-micron structures;
   placing the sample on the sample holder adjacent the plasmonic layer;
   illuminating the sample and sample holder and capturing at least one color digital image thereof with an optical microscope, the illumination stimulating surface plasmon resonance and the sample positioned at least partially within the associated evanescent sensing field, the at least one digital image comprising a plurality of pixels which represent a two dimensional region of the sample, wherein at least one localized structural property of the sample is visible in the image based on the color of received light captured in the at least one digital image; and
   processing the at least one digital image, based on the received color information to selectively identify said structure on the basis of color differentiation and/or morphology differentiation,
   wherein, in the received digital image, the localized structural property of the sample is a localized refractive index.

2. The method of claim 1, wherein processing the at least one image includes providing an output indicating the identification of the structure.

3. The method of claim 1, including filtering the image to selectively process a portion of the image on the basis of color information contained in the received image.

4. The method of claim 1, wherein the at least one image includes a plurality of pixels, and said method includes segmenting the at least one image based on a color of received light captured in the image.

5. The method of claim 4, wherein segmenting the at least one image includes one or more of:
   identifying one or more subsets of pixels within an image based at least partly on color;
   grouping pixels into features representing a structure on the sample based on correlation between a pixel and at least one neighbouring pixel.

6. The method of claim 1, including one or more of:
   determining a color distribution of the received image;
   determining a color histogram of the received image;
   performing spectral analysis of at least part of the received digital image.

7. The method of claim 1, including performing a feature extraction method to identify one or more structures in the image.

8. The method of claim 1, including processing the digital image with an image recognition system.

9. The method of claim 8, wherein the image recognition system is an artificial neural network.

10. The method of claim 1, wherein, in the received digital image, the localized structural property of the sample is a localized refractive index.

11. The method of claim 1, wherein a structure in the sample with a given refractive index appears as a corresponding color or color range in the image.

12. The method of claim 1, wherein the sample is a biological sample.

13. The method of claim 1, including identifying a feature within said structure based on color differentiation.

14. The method of claim 1, including identifying a feature within said structure based on morphology differentiation.

15. The method of claim 1, including identifying a feature within said structure based on a combination of color differentiation and morphology differentiation.

16. The method of claim 1, wherein receiving at least one digital image of a sample includes receiving more than one image of the sample captured with one or more of the following differences:
- different illumination spectrum;
- different illumination polarisation;
- different magnification.

17. The method of claim 11, wherein the structure includes one or more of a neoplastic cell, cancer cell, healthy cell, cell of a given type, cell state, parasite, group of cells, abnormal cell, infected cell, tissue of a given type.

18. A system comprising a data processing system, said system being adapted to perform the method of claim 1.

* * * * *